United States Patent
Lob et al.

[11] Patent Number: 6,136,035
[45] Date of Patent: Oct. 24, 2000

[54] MODULAR JOINT PROSTHESIS

[75] Inventors: Günter Lob, München; Hans-Joachim Fischer, Berlin; Gerd Steür, Berlin; Curt Kranz, Berlin, all of Germany

[73] Assignee: Merck Patent GmbH, Germany

[21] Appl. No.: 08/836,640

[22] PCT Filed: Nov. 20, 1995

[86] PCT No.: PCT/DE95/01655
§ 371 Date: Jul. 25, 1997
§ 102(e) Date: Jul. 25, 1997

[87] PCT Pub. No.: WO96/15739
PCT Pub. Date: May 30, 1996

[30] Foreign Application Priority Data

Nov. 19, 1994 [DE] Germany .................. 44 42 204

[51] Int. Cl.[7] ................ A61F 2/36; A61F 2/30
[52] U.S. Cl. ............................ 623/23; 623/18
[58] Field of Search .................. 623/23, 22, 16, 623/19, 18

[56] References Cited

U.S. PATENT DOCUMENTS

| 4,704,128 | 11/1987 | Frey | 623/23 |
|---|---|---|---|
| 4,878,917 | 11/1989 | Kranz et al. | 623/18 |
| 5,002,578 | 3/1991 | Luman | 623/23 |
| 5,080,676 | 1/1992 | May | 623/20 |
| 5,562,666 | 10/1996 | Brumfield | 606/64 |
| 5,591,233 | 1/1997 | Kelman et al. | 623/16 |

FOREIGN PATENT DOCUMENTS

| 0290735A1 | 3/1988 | European Pat. Off. . |
| 0669116A1 | 1/1995 | European Pat. Off. . |

Primary Examiner—Mickey Yu
Assistant Examiner—Alvin Stewart
Attorney, Agent, or Firm—Venable; George H. Spencer; Robert Kinberg

[57] ABSTRACT

A modular hip joint prosthesis is assembled from a head section having a connection for the ball of the joint and from a shaft section. The shaft section is joined by a insert connection to the head section, and provision is made for fixing the insert connection. The insert connection is situated in the region of Shenton's arc. The respective contours, in longitudinal section, of the head and shaft sections in the region of the connection merge smoothly, without any substantial change in direction, irrespective of the relative mutual alignments of the sections at any given time, with the exception of a gap in the immediate vicinity of the connection.

19 Claims, 7 Drawing Sheets

MODULAR JOINT PROSTHESIS

FIELD OF THE INVENTION

The invention relates to a modular joint prosthesis comprising a head part including a connection for a ball of the joint; a shaft part connectable to the head part by an insert connection; and means for locking the insert connection.

Joint prostheses are produced in the most various shapes and sizes, particularly as hip joint prostheses, to create good adaptation to the anatomical conditions of a given patient.

By means of a multi-part embodiment with nonpositive connection of the corresponding individual parts in the proximal region, the adaptation can be accomplished optimally. At the same time, positioning of the joint head is possible regardless of the shaft diameter.

From European Patent Disclosure EP-B1 0 243 298, a kit for a shaft prosthesis is known, which has a head part that can be provided with a joint ball, an end part anchored in the bone, and an intermediate part that can be positioned between the two. All the parts have conical bores or complementary pegs, and as a result the prosthesis can be assembled by making conical insert connections. The head part and intermediate part each have an axial through bore.

When the individual parts are put together, the corresponding bores are aligned axially in the direction of the shaft. The individual parts of the prosthesis are put together using a tie rod that transmits a force in the axial direction and that penetrates both the head part and succeeding shaft parts and can be screwed into the threaded bore of the end part. As a result, the head part, or the intermediate part, and the end part are firmly tightened against one another, so that loosening of the individual parts of the prosthesis from the mechanical strain during use need not be feared.

The prosthesis described in EP 0 243 298, however, is not bent and is, therefore, not optimally adapted to the anatomy of the hip joint. Furthermore, in other previously known hip joint prostheses, a universal version, that is, one that can be used for the majority of disease cases to be expected, is unattainable.

SUMMARY OF THE INVENTION

In view of the deficiencies in the prior art, it is the object of the invention to create a modular hip joint prosthesis of the generic type referred to at the outset, which by the embodiment of its individual parts offers the possibility of producing a universal usable prosthesis.

The above and other objects are accomplished according to the invention by the provision of a modular hip joint prosthesis comprising: a head part, including a connection for a ball of the joint; a shaft connectable to the head part in a connection region having a curved contour region, in longitudinal section, corresponding to Shenton's arc, the head part including a distal region and the shaft part including a proximal region that together define an insert connection having peripheral edges separated by a gap in the curved contour region; and means for locking the insert; wherein the head part and the shaft part have respective contours in the connection region, in longitudinal section, which merge with one another without substantially changing direction, regardless of a particular relative alignment of the head and shaft parts, except for the gap in the connection region.

The invention encompasses the recognition that by embodying a hip joint prosthesis in two parts, favorable conditions are present for universal use of it, if the resultant structural form, regardless of the type of assembly, is adapted to the form of a modern standard prosthesis. This has been attained with the provisions of the invention, regardless of the alignment of the shaft end relative to the head part. Care is taken particularly to assure that the insert connection for connecting the shaft parts is located in a region which, when it is adapted to the evacuated marrow space, does not require any recesses or widened portions in order to be received. With the provisions of the invention, a shaft prosthesis can be created which enables it to be designed for an individual patient while still having the usual dimensions (and particularly with precise adaptation to the evacuated interior of the bone). This can be done with a minimum number of component units that have to be kept on hand, and can thus be done economically.

At the same time, this is also a prerequisite for being able to produce a hip joint prosthesis that can be implanted on the left side, having all intermediate positions also be possible, using a right-side implantable prosthesis, merely by pivoting the prosthesis head part 180° about the longitudinal axis of the insert connection. Because the shaft region under the connecting location widens conically, once again a secure introduction of force into the bone is assured, so that the connecting region itself is relieved.

With the provisions of the invention, even extremely long prostheses can be put together in various configurations; because of the possibility of optimal shape adjustment by rotation in the connecting region, the optimal seating of each prosthesis assembly in anatomically correct form is assured. With the means of the invention, using a prosthesis kit, it is accordingly possible to provide an individual accurate fit of a prosthesis made for an individual patient.

In accordance with a preferred embodiment of the invention, the hip joint prosthesis provided for cementless implantation can be put together from a head part and a shaft part. A conical peg is provided on the proximal end of the shaft part, and a recess of corresponding dimensions is provided on the distal end of the head part, forming an insert connection once the joint prosthesis has been put together. The head part is divided up into a base and a connection peg intended to carry the ball of the joint. The cross-sectional profile of the base of the head part is embodied substantially elliptically, and the long half-axis of the cross-sectional ellipse decreases continuously in the distal direction.

One profiled section each, comprising axially extending ribs with rounded outer edges, is provided on the dorsal and frontal side faces of the head part. This advantageously creates a large surface area, which promotes fixation of the prosthesis by the ingrowth of bone material.

Preferably, the base of the head part has a longitudinal sectional profile, in a dorsal/frontal view, that widens in the proximal direction and is bounded on its lateral side by two straight lines forming an obtuse angle and on its medial side by a concave arc region. The distally located straight line of the pair of straight lines and the arc segment continue in a respective straight line, which bound the distally conically tapering longitudinal sectional profile of a proximal portion of the flat located below the insertion cone.

The straight lines of the pair of straight lines of the head part profile are of different lengths and each has an inclination in the direction of the center axis of the head part, and the shorter straight line is located on the distal end of the head part.

In a favorable further feature of the invention, a ratio of the lengths of the straight lines in a range from 6 to 10 is provided.

The proximal end of the shaft part is embodied as a straight truncated cone tapering in the distal direction, which on its distal end changes over, without shoulders, into a substantially cylindrically embodied shaft portion. The diameter of the proximal circular face of the truncated cone is equivalent to the length of the long half-axis of the total elliptical cross-sectional area on the distal end of the head part. However, it is greater than the length of the short half-axis of this cross-sectional area. The resultant slight protrusion of the shaft part from the dividing point creates additional anchoring of the shaft part when the hip joint prosthesis is implanted, and this favorably counteracts loosening of the shaft in the event that a medically necessary replacement of the head part has to be performed.

For the height of the truncated cone, a value of one-fourth to one-fifth the effective shaft length is favorable.

In another further feature of the invention, the cylindrical portion of the shaft part has profiling in the form of axially extending ribs, whose peripheral edges are rounded. The ribs are distributed uniformly on the circumference of the shaft. The cylindrically embodied portion of the shaft part has a frontally oriented uniform curvature, and thus advantageously creates preconditions for adapting the prosthesis to the anatomy of the upper thigh bone.

In another advantageous embodiment of the invention, the shaft part has a longitudinal bore extending in the direction of the shaft axis. This longitudinal bore terminates on its distal end in at least one lateral opening in the shaft wall. The lateral opening is embodied as an oblong slot. It serves on the one hand to equalize pressure on insertion of the hip joint prosthesis, and on the other hand favorably allows the outflow of medications, which can be introduced by placing a medication dispenser on the distal end of the longitudinal bore of the shaft part. The mean diameter of the longitudinal bore therefore has a value which enables the positioning of the medication dispenser in the vicinity of the wall openings in the distal region of the shaft part.

In another further feature of the invention, a through bore extending crosswise to the shaft axis is provided between the distal end of the longitudinal bore of the shaft part and the distal shaft end, in order to receive further fixation means. The diameter of the transverse bore is selected such that the possibility exists of inserting a Küntscher intermedullary nail. The use of fixation means on the distal shaft end of the hip joint prosthesis increases the security against twisting and the axial load-bearing capacity of the prosthesis.

Since the bending stress acting on the endoprosthesis is not constant over time, but instead is subject to fluctuations in amount and direction depending on the natural stress conditions of the endoprosthesis, microscopic motions occur between the peg and the bore. These microscopic motions, in combination with the local peak tensions occurring at the edge of the mouth of the bore, can cause abrasion of material and thus premature wear, which is also called fretting.

The local peak tensions occurring at the edge of the mouth of the bore are due to the fact that given a largely rigid peg reception, if the peg and bore are offset because of a bending stress, the effective tension-absorbing contact area is reduced. In an extreme case, the peg touches the inner wall of the bore only indirectly at the edge of the mouth and on the opposite end on the bottom of the bore.

In an advantageous further variant of the invention, with its own patentable significance, the elasticity of the shaft element is therefore increased shortly before the end of the mouth of the conical bore, so that the inner wall of the bore, in the event of a bending stress on the endoprosthesis and thus attendant with staggering of the longitudinal axes of the peg and the bore, adapts to the position of the leg and with the jacket face of the peg forms a sufficiently large tension-absorbing contact area. The immediate end of the cone maintains the same wall thickness, however, in order to preserve adequate strength here. Therefore the introduction of force in the end region of the cone is distributed over a greater length, thus avoiding excessive strain in the immediate region of the mouth.

To that end, the head part or shaft part with the conical bore, on its outside at the level of the bore, has a notch that extends at least partway around relative to the longitudinal axis of the bore. As a result, the wall thickness of the peg receptacle is reduced, which increases its resilience. Upon a bending stress on the joint prosthesis and a consequent staggering of the peg and bore relative to one another, the inner contour of the bore therefore adapts to the position of the peg, and the tension-absorbing contact area between the peg and the bore is reduced only slightly, which results in a lesser mechanical stress at the edge of the mouth of the bore and thus reduces mechanical wear.

By the weakening of the material as a result of the notch, the introduction of force takes place not initially as a maximum peak at the end of the mouth of the conical bore but rather in evened-out fashion over the entire contact area of the peg and bore. Because of this evening out of the force introduction, the maximum value for the mechanical tension is reduced, and an overload on the material is thus prevented.

BRIEF DESCRIPTION OF THE DRAWINGS

Advantageous further features of the invention are described in further detail below along with the description of the preferred embodiment of the invention, in conjunction with the drawings. Shown are.

DESCRIPTION OF THE PREFERRED EMBODIMENT

Figure 1:
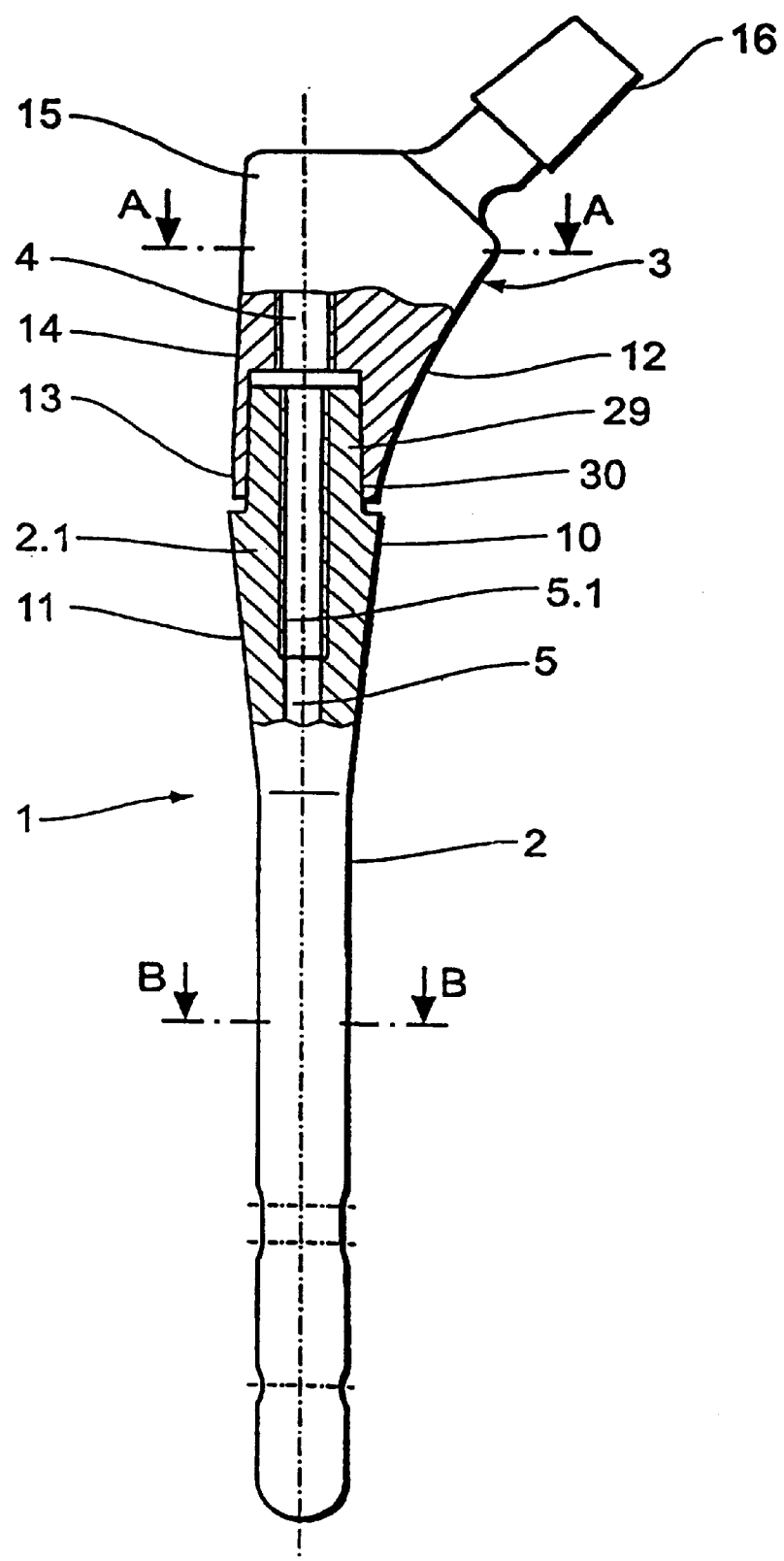
FIG. 1, a dorsal and frontal view in fragmentary longitudinal section of a preferred embodiment of the invention.
Figure 2:
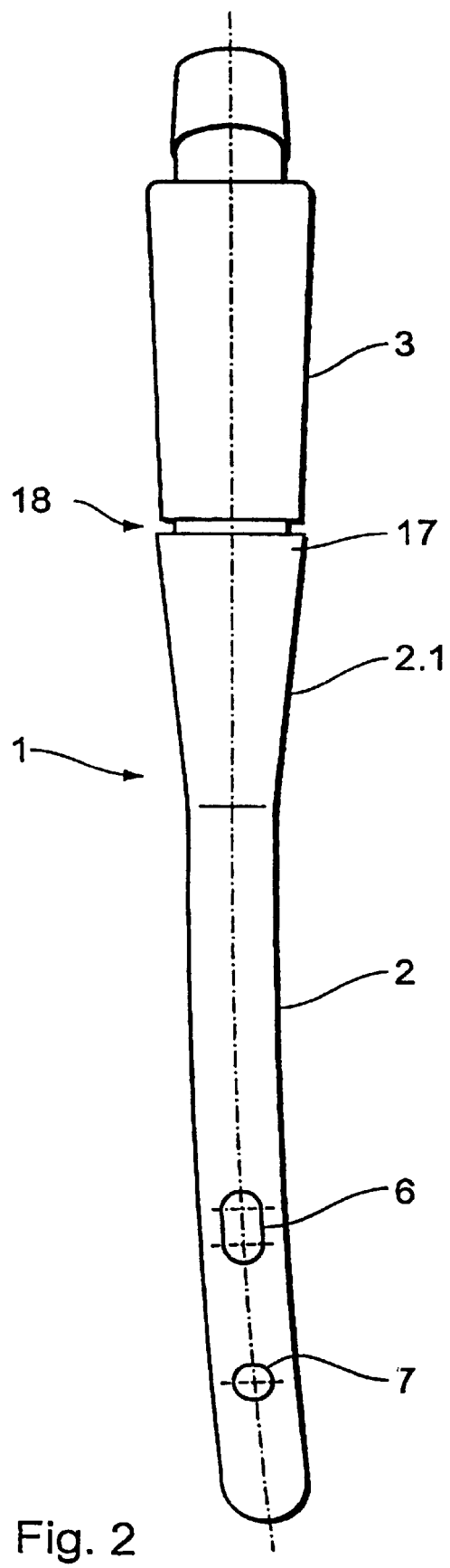
FIG. 2, a side view of the embodiment of the invention shown in FIG. 1.

In FIGS. 1 and 2, the preferred embodiment of the invention is shown in fragmentary longitudinal section, in a dorsal/front view and in a lateral view, respectively. The hip joint prosthesis 1 comprises a shaft part 2 and a head part 3, which are taken from a kit for modular hip joint prostheses in which essentially identically embodied head parts and shaft parts of various sizes are provided. The particular individual elements 2, 3 selected can preferably be connected to one another by putting together their respective proximal or distal ends that have corresponding conical pegs 29 or recesses 30. The requisite stability of the insert connection is assured by means (not shown)—preferably embodied as a tie rod. The respective shaft part 2 is embodied as a hollow shaft, and the axially extending longitudinal bore 5 on its proximal end portion is embodied as a threaded bore 5.1. The tie rod (not shown) is passed through a cylindrical channel 4 in the head part 3, located on the same axis as the longitudinal bore 5 in the shaft part 2, and screwed into the threaded bore 5.1 of the shaft part 2.

The base 15 of the head part 3 has a longitudinal sectional profile, in a dorsal/frontal view, that widens in the proximal direction and is bounded on its lateral side by two straight lines 13, 14 forming an obtuse angle and on its medial side by a concave arc region 12. The distally located straight line 13 of the pair of straight lines 13, 14 and the arc segment 12 continue in a respective straight line 10, 11, which bound the distally conically tapering longitudinal sectional profile of a proximal portion 2.1 of the flat 2 located below the insertion cone.

It can be seen that in the connecting region of the side view, shown in FIG. 2 the side lines merge without essentially changing pitch from the proximal portion 2.1 of the shaft part 2 to the head part 32. In fact, this is true, independent of the relative angular orientation of the shaft part 2 and the head part 3; thus, the outer surface of the prosthesis appears without remarkable discontinuities, regardless of such angular orientation. In this way, first—with a curved shaft part—a left-side or right-side prosthesis is selectively created, without reducing the continuity of the shape contour. However, since intermediate positions can be attained without difficulty while at the same time preserving the optimal contour course, the seat of the prosthesis can be adapted very precisely to the individual conditions. This is also true for long shafts, which are available in various lengths as a substitute for a bone nail. Thus with a minimum number of basic elements, it is possible to meet a maximum number of needs in entirely different cases.

The straight lines 13, 14 have different lengths and each has an inclination in the direction of the center axis of the head part 3, with the shorter straight line 13 located on the distal end of the head part 3. A value in the range from 6 to 10 is contemplated for the ratio of lengths of the straight lines 13, 14.

As shown in FIG. 2 the proximal end of the shaft part 2, is embodied as a straight truncated cone 2.1, tapering in the distal direction, which on its distal end changes over without shoulders into a shaft portion embodied essentially cylindrically, and having a continuous curvature in the frontal direction. This kind of shaping on the proximal shaft end advantageously assures a firm seat of the shaft part in the marrow space of the upper thigh bone. For the height of the truncated cone 2.1, one-fourth to one-fifth of the effective length of the shaft part 2 (that is, of the shaft portion to be introduced into the marrow space) is favorable. The diameter of the proximal circular area of the truncated cone 2.1 is equivalent to the length of the long half-axis of the total elliptical cross-sectional area on the distal end of the head part 3. However, it is greater than the length of the short half-axis of the aforementioned cross-sectional area. The resultant slight protrusion 17 of the shaft part 2 at the dividing point 18 creates additional anchoring of the shaft part 2 when the hip joint prosthesis 1 is implanted, which favorably counteracts loosening of the shaft in the event that a medically necessary replacement of the head part has to be performed.

The opening 6 in the wall of the shaft part 2 forms the distal end of the longitudinal bore (see reference numeral 5 of FIG. 1) of the shaft of the hip joint prosthesis 1. It is embodied as a longitudinal slot and serves on the one hand to allow the outflow of medication form a medication dispenser (not shown) positioned at the end of the longitudinal bore, and on the other hand to equalize pressure when the hip joint prosthesis 1 is introduced by its shaft part 2 into the prepared marrow space of an upper thigh bone.

The through bore 7 on the distal end of the prosthesis shaft extends crosswise to the axis of the shaft part 2. This bore is intended to receive a fixation means, such as a locking nail, and is adapted in its diameter to the possible dimensions of the nail. The use of additional fixation means advantageously increases the security against twisting and the axial load-bearing capacity of an implanted prosthesis.

It will be appreciated that according to the invention, even extreme shaft lengths, for applications in which until now nails had to be employed, can be provided as shaft prostheses.

Figure 3:
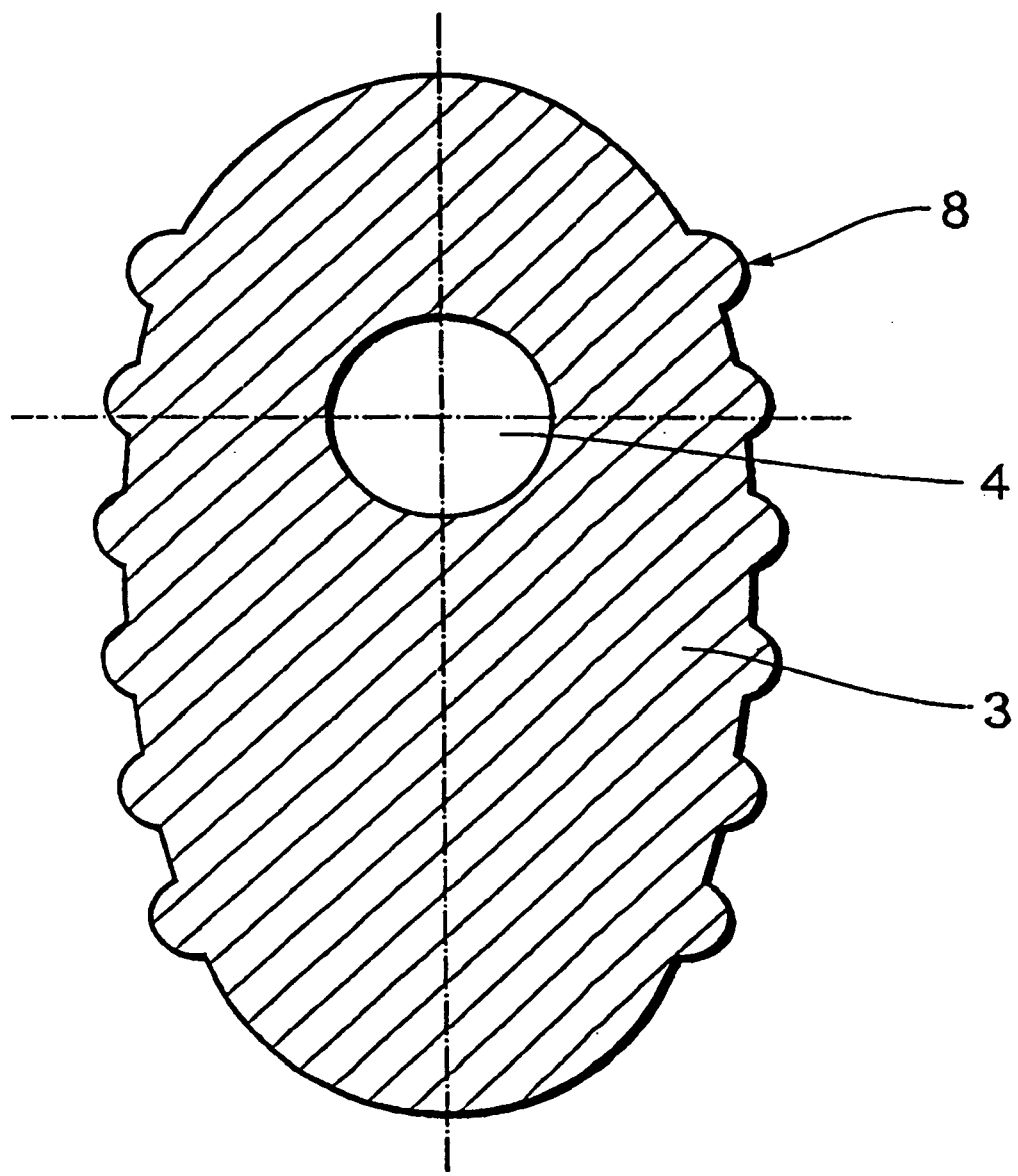
FIG. 3, a sectional view taken along the line A . . . A of FIG. 1.
Figure 4:
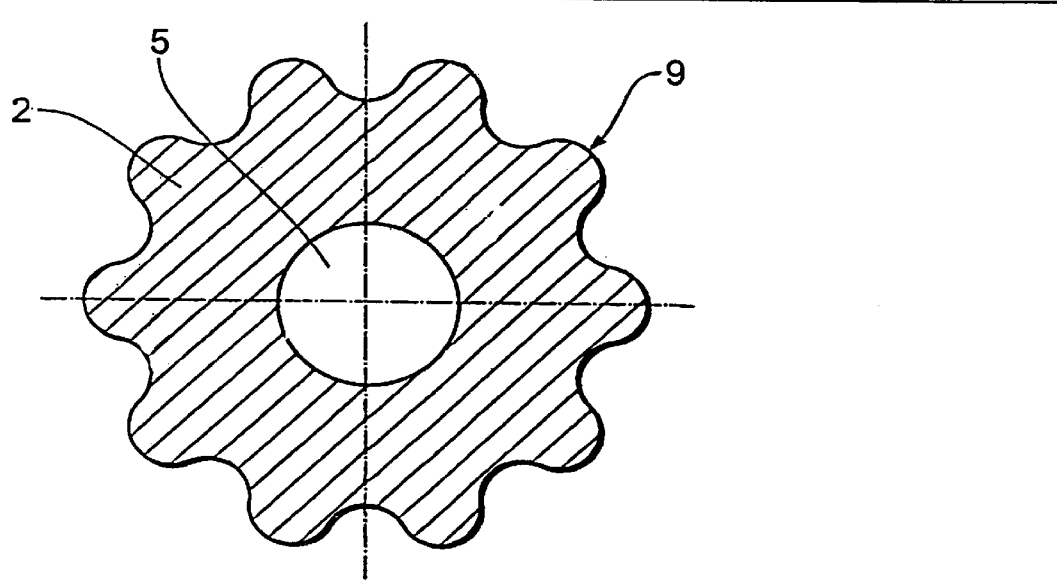
FIG. 4, a further section taken along the line B . . . B of FIG. 1.

In FIGS. 3 and 4, a cross-sectional profile of the head part 3 (section along the line A . . . A of FIG. 1) and a cross-sectional profile of the shaft part 2 (section along the line B . . . B of FIG. 1), respectively, are shown. The ribs 8, 9 extending axially, respectively on the broad sides of the head part 3 and on the periphery of the shaft part 2, are bounded peripherally by circular arcs. The through bore in the elliptical cross-sectional profile of the head part 3 is shown at 4, and the central longitudinal bore of the shaft part 2 is shown at 5.

Figure 5:
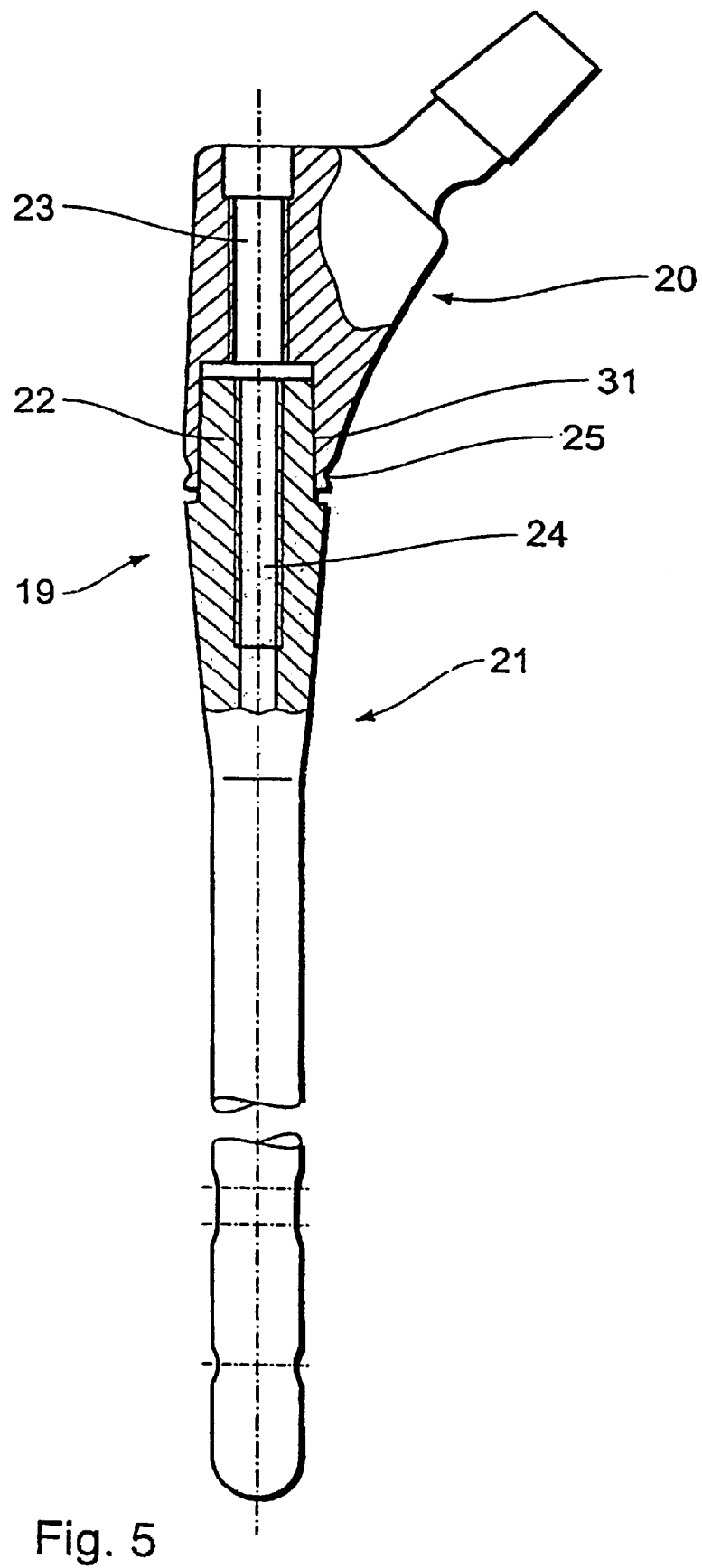
FIG. 5, a modification of the joint prosthesis shown in FIG. 1, in a fragmentary sectional view.

The joint prosthesis 19 shown in cross section in FIG. 5 is a further improvement of the joint prosthesis shown in FIG. 1; the joint prosthesis 19 shown here has increased mechanical strength and reduced wear.

The joint prosthesis 19 shown—like the joint prosthesis shown already in FIG. 1—especially comprises a head part 20 and a shaft part 21 connected to it by a cone connection. The mechanical connection of the head part 20 and shaft part 21 is accordingly accomplished nonpositively, in that a conical peg 22 formed onto the shaft part 21 is inserted into a conical bore 31 disposed in the head part 20 and with this bore forms a press fit. To brace the head part 20 and shaft part 21 against one another, a tie rod is used, which passes through a channel 23 in the head part 20 and screwed into a threaded bore 24 in the shaft part 21.

In such joint prostheses, the problem exists that upon a bending stress on the joint prosthesis, relatively high mechanical tensions occur at the edge of the mouth of the conical bore. The peak mechanical tensions at the edge of the mouth of the conical bore are due to the fact that upon a bending stress on the joint prosthesis 19, the peg 22 and bore become offset from one another, which causes a decrease in the effective tension-absorbing contact area between the peg 22 and bore.

In an extreme case, the peg 22 now touches the inner wall of the bore only unilaterally, respectively directly at the edge of the mouth and on the opposed side directly on the bottom of the bore. The reduction in the effective tension-absorbing contact area therefore creates relatively high mechanical tensions, particularly at the edge of the mouth of the bore.

Since the bending stress acting on the joint prosthesis 19 is not constant over time but instead is subject to fluctuations in amount and direction depending on the natural stress states of the joint prosthesis 19, microscopic motions occur between the peg 22 and the bore. These microscopic motions, in combination with the local peak tensions occurring at the edge of the mouth of the bore, can cause abrasion of material and thus premature wear, which is also called fretting.

To reduce these wear phenomena, the head part 20—in contrast to the joint prosthesis shown in FIG. 1—therefore has a notch 25, encompassing it on the outer wall near the lower end with regard to the longitudinal axis of the bore. As a result of this notch 25, the wall thickness of the head part 20 is reduced, thus increasing the resilience of the peg receptacle in the face of an offset of the peg 22. If the peg 22 is offset relative to the bore as the result of a bending stress on the joint prosthesis 19, then the peg receptacle—that is, the internal contour of the bore—yields to the peg 22 and adapts to the altered position of the peg 22.

By this elastic adaptation of the peg receptacle, the effective tension-absorbing contact area between the bore and peg is reduced only insubstantially, even in the event of a bending stress on the joint prosthesis 19, which leads to a reduction in the mechanical stress occurring at the edge of the mouth of the bore and reduces the wear on the joint prosthesis 19.

Figure 6:
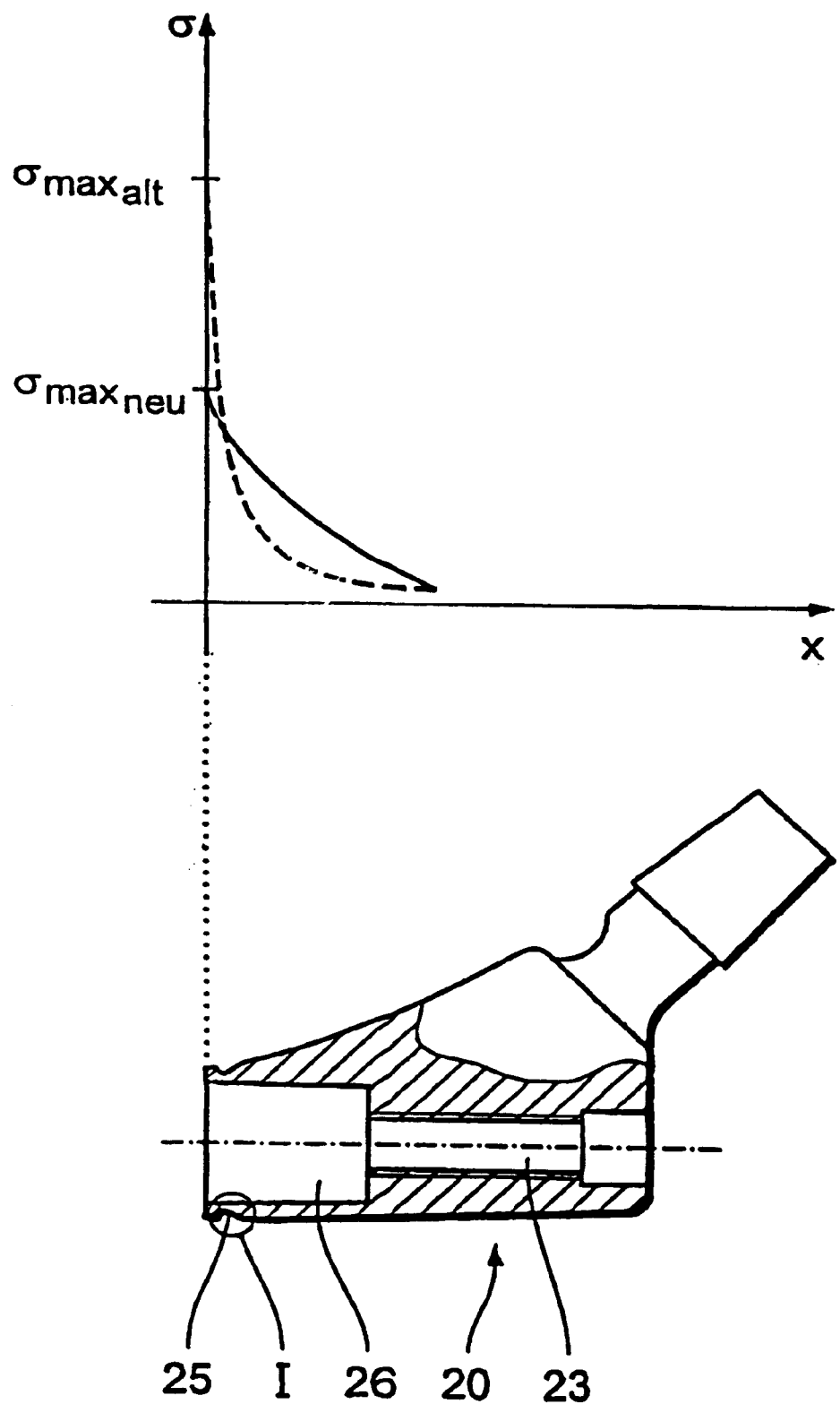
FIG. 6, again in a fragmentary sectional view, the head part of the joint prosthesis shown in FIG. 5.

The cross-sectional view shown in FIG. 6 of the head part 20 of the joint prosthesis shown in FIG. 5 clearly shows the shape and disposition of the notch 25 in the head part 20. The notch 25 initially has a depth that increases along the longitudinal axis of the head part 20 toward its end.

On the one hand, it is thereby attained that the peg receptacle—that is, the internal contour of the bore 26—adapts well to the altered position of the peg in the event of relatively slight bending stresses on the joint prosthesis and correspondingly slight offsets of the peg and bore 26, and this, despite the offsetting of the peg and bore 26, leads to a relatively large effective tension-absorbing contact area between the peg and bore 26, and hence to a reduction in the mechanical stress.

On the other hand, because of the resilience of the peg receptacle, which decreases toward the top along the longitudinal axis of the head part 20, it is assured that the peg receptacle—that is, the internal contour of the bore 26—yields only insubstantially, in response to major bending stresses of the joint prosthesis, which yielding is indispensable for a secure, largely play-free guidance of the peg. The peg receptacle is accordingly relatively soft in the face of relatively slight bending stresses, which leads to a reduction in the mechanical tensions at the edge of the mouth of the bore 26, but becomes harder as the bending stress increases, which serves the purpose of secure guidance of the peg.

The notch 25 on the one hand leads to a reduction in the mechanical tension at the edge of the mouth of the bore 26. On the other hand, however, the notch 25 represents a mechanical weak point in the head part 20, which involves the risk of crack formation and consequent mechanical failure of the joint prosthesis. To reduce this risk, the notch 25 has a smooth shape, without protruding or indented corners or edges. Thus on its upper end, the notch 25 terminates smoothly in the outer wall of the head part 20, without forming any kink or even a shoulder. As a result, the notch tensions that occur in the notch 25, and hence the danger of crack formation, are reduced.

FIG. 6 also shows the course of the mechanical stress, occurring in the peg receptacle, along the longitudinal axis of the bore 26. The dashed line, for comparison, shows the course of tension in the joint prosthesis shown in FIG. 1, while the solid line shows the course of mechanical tension in the above-described joint prosthesis having the notch 25.

In the joint prosthesis of FIG. 1, the course of the mechanical tension along the longitudinal axis of the bore (not labeled in FIG. 1) corresponding to bore 26 is very highly nonlinear. Thus, the tension in the upper region of the bore 26 is relatively slight, while in the vicinity of the edge of the mouth it increases up to the value $\delta_{max,old}$.

In the above-described joint prosthesis, the course of tension along the longitudinal axis of the bore 26 is conversely substantially more uniform, which advantageously results in a substantially lesser maximum tension $\delta_{max,new}$.

Figure 7:
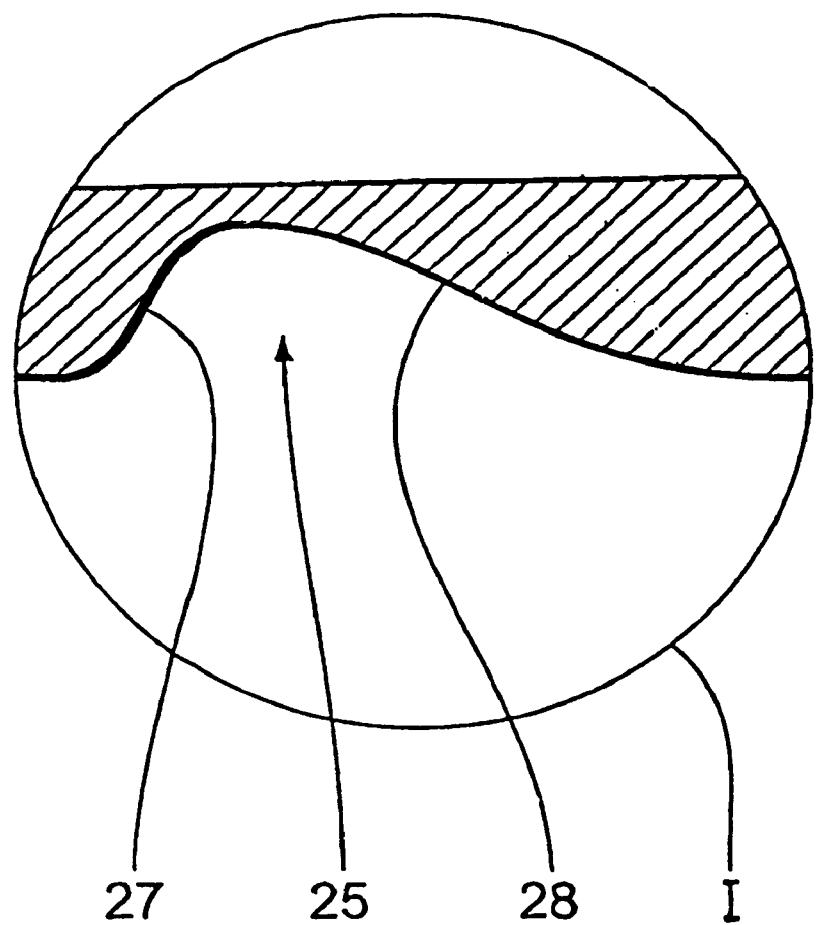
FIG. 7, a detail of FIG. 6.

The form of the notch 25 can be seen in more detail from FIG. 7, which shows the detail I of FIG. 6. This illustration clearly shows that the notch 25 is asymmetrical and has a depth that increases toward the end of the peg. Accordingly the notch 25 has two flanks 27, 28 of different pitch; the flank 27 toward the end of the peg extends relatively steeply and has only a slight length, while the flank 28 remote from the end of the peg extends relatively shallowly but is elongated and terminates at the peg wall.

The invention is not limited in its realization to the preferred exemplary embodiment described above. On the contrary, a number of variants are conceivable, which make use of the provisions described, even in fundamentally different types of embodiments.

What is claimed is:

1. A modular hip joint prosthesis, comprising:

a head part, including a connection for a ball of the joint;

a shaft part connectable to the head part in a connection region having a curved contour region, in longitudinal section, corresponding to Shenton's arc, the head part including a distal region and the shaft part including a proximal region that together define an insert connection having peripheral edges separated by a gap in the curved contour region; and means for locking the insert connection;

wherein the head part and the shaft part have respective contours in the connection region, in longitudinal section, which merge with one another without substantially changing direction, regardless of a particular relative alignment of the head and shaft parts, except for the gap in the connection region; and wherein:

the head part and/or the shaft part has a conical bore on its underside;

the shaft part, on its top side, has a conical peg adapted to the conical bore, for connection to the head part or a further shaft part; and a notch in the head part and/or the shaft part, extending all the way around on the outer wall in the vicinity of the end of the mouth of the conical bore, which notch reduces the mechanical stress occurring due to a bending stress at the edge of the mouth of the conical bore.

2. The modular hip joint prosthesis of claim 1, wherein the shaft part includes a region that widens frustoconically toward the head part in a proximal portion of the shaft part in the connection region.

3. The modular hip joint prosthesis of claim 2, wherein the inclination of the frustoconically widening region of the shaft part is continued by the inclination of the curved contour region of the head part in the connection region.

4. The modular hip joint prosthesis of claim 1, wherein a proximal region of the head part has a longitudinal sectional profiled in a dorsal/frontal view that widens in the proximal direction and is bounded on its lateral side by two straight lines forming an obtuse angle and on its medial side by a concave arc segment, wherein the distally located straight line of the two straight lines and the arc segment continue in respective straight lines, which bound the distally conically tapering longitudinal sectional profile of a proximal portion of the shaft part located below an insertion cone located on the proximal end of the shaft part and forming part of the insertion connection.

5. The modular hip joint prosthesis of claim 1, wherein a base portion of the head part has a substantially elliptical cross-sectional profile.

6. The modular hip joint prosthesis of claim 5, wherein the long half-axis of the cross-sectional ellipse decreases continuously in the distal direction.

7. The modular hip joint prosthesis of claim 1, wherein the proximal end of the shaft part constitutes an insertion cone, and wherein the proximal portion of the shaft part below the insertion cone is embodied as a truncated cone, which tapers distally down to the terminal diameter of the shaft part.

8. The modular hip joint prosthesis of claim 7, wherein the length of the truncated cone is equivalent to one-fourth to one-fifth the effective shaft length.

9. The modular hip joint prosthesis of claim 7, wherein a portion of the shaft part adjoining the distal end of the truncated cone has a uniform curvature in the frontal direction.

10. The modular hip joint prosthesis of claim 1, wherein the shaft part has a longitudinal bore extending in the direction of the shaft axis.

11. The modular hip joint prosthesis of claim 10, wherein the longitudinal bore ends on its distal end in at least one lateral opening in the shaft wall.

12. The modular hip joint prosthesis of claim 11, wherein the lateral opening has the form of an oblong slot.

13. The modular hip joint prosthesis of claim 10, wherein the distal end of the shaft part contains a transverse bore, for receiving an additional fixation means.

14. The modular hip joint prosthesis of claim 1, further including a profile comprising axially extending ribs with rounded outer edges on the broad sides of a base portion of the head part.

15. The modular hip joint prosthesis of claim 1, wherein the shaft part has a longitudinal profiling comprising ribs with rounded edges.

16. The modular hip joint prosthesis of claim 15, wherein the ribs are distributed uniformly over the circumference of the shaft part.

17. The modular hip joint prosthesis of claim 1, wherein the depth of the notch increases partway along the longitudinal axis of the bore toward the end of the head part.

18. The modular hip joint prosthesis of claim 1, wherein the notch is shaped such that, upon occurrence of a bending stress, the mechanical tension at the edge of the mouth of the conical bore along the longitudinal axis of the bore is essentially uniform, at least in the vicinity of the mouth of the conical bore.

19. The modular hip joint prosthesis of claim 4, wherein the proximally located straight line of the two straight lines is inclined, in the proximal direction, toward the longitudinal axis of the prosthesis.

* * * * *